United States Patent
Maranta et al.

(10) Patent No.: US 8,338,666 B2
(45) Date of Patent: *Dec. 25, 2012

(54) POLYPEPTIDES HAVING ACETYLXYLAN ESTERASE ACTIVITY AND POLYNUCLEOTIDES ENCODING SAME

(75) Inventors: Michelle Maranta, Davis, CA (US); Kimberly Brown, Elk Grove, CA (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,177

(22) Filed: Mar. 1, 2012

(65) Prior Publication Data

US 2012/0149078 A1 Jun. 14, 2012

Related U.S. Application Data

(63) Continuation of application No. 12/327,347, filed on Dec. 3, 2008, now Pat. No. 8,129,590.

(60) Provisional application No. 60/992,995, filed on Dec. 6, 2007.

(51) Int. Cl.
*C12N 15/31* (2006.01)
*C12N 15/82* (2006.01)
*C12N 15/10* (2006.01)
*A01H 5/00* (2006.01)

(52) U.S. Cl. ........ 800/288; 800/284; 800/295; 800/278; 435/320.1; 435/468; 536/23.1; 536/23.2; 536/23.7

(58) Field of Classification Search .......... None
See application file for complete search history.

(56) References Cited

U.S. PATENT DOCUMENTS

| 5,681,732 A | 10/1997 | De Graaff et al. |
| 5,763,260 A | 6/1998 | De Graaff et al. |
| 8,129,590 B2 * | 3/2012 | Maranta et al. ............... 800/288 |

FOREIGN PATENT DOCUMENTS

| EP | 0507369 | 3/1992 |
| JP | 2001054383 A | 2/2001 |
| WO | 2005001036 | 1/2005 |
| WO | 2009073709 A1 | 12/2008 |

OTHER PUBLICATIONS

Written Opinion of the International Searching Authority for PCT/US2008/085380.
Margolles-Clark et al., Accetyl xylan esterase from *Trichoderma reesei* contains an active-site serine residue and a cellulose-binding domain, 1996, Eur. J. Biochem. 237: 553-560.
Henrissat B., A classification of glycosyl hydrolases based on amino acid sequence similarities, 1991, Biochem. J. 280: 309-316.
Henrissat et al., Updating the sequence-based classification of glycosyl hydrolases, 1996, Biochem. J. 316: 695-696.
Sundberg et al, 1991, Biotechnol. Appl. Biochem. 13: 1-11.

* cited by examiner

*Primary Examiner* — Brent T Page
(74) *Attorney, Agent, or Firm* — Robert L. Starnes; Eric J. Fechter

(57) ABSTRACT

The present invention relates to isolated polypeptides having acetylxylan esterase activity and isolated polynucleotides encoding the polypeptides. The invention also relates to nucleic acid constructs, vectors, and host cells comprising the polynucleotides as well as methods of producing and using the polypeptides.

20 Claims, 4 Drawing Sheets

Fig. 1A

```
 937  GGCCCAACCTCGTCGGCATCTACGGCAGCGGCGTCACCCACAACATCCCCGTCAACGGCGCCAACGACATG
       E  W  F  G  I  T  G  N  P  T  T  T  S  T  S  A  T  V  P  T  T  T  S  S
1009  GAATGGTTCGGCATCACCGGCAACCCGACCACCACCTCGACCTCTGCTACTGTGCCTACTACCACGAGCAGC
       P  G  T  T  S  T  S  A  P  V  T  T  T  S  R  A  P  P  P  T  Q  T
1081  CCCGGCACCACCTCGACCAGCGCCCCGGTCACCACGACCAGCTCGCGGCTCCTCCCCTCCTACTCAGACT
       C  I  P  V  P  R  N  G  Q  C  G  G  I  T  W  G  G  C  T  V  C  E  A  P
1153  TGTATACCCGTCCTCGTTGGGGCAGTGCGGCGGCATCACCTGGGGAGGCTGCACCGTCTGCGAGGCGCCG
       Y  T  C  Q  K  L  N  D  W  Y  S  Q  C  L  *
1225  TACACTTGCCAGAAGCTGAATGATTGGTACTCTCAGTGCCTGTAA
```

POLYPEPTIDES HAVING ACETYLXYLAN ESTERASE ACTIVITY AND POLYNUCLEOTIDES ENCODING SAME

CROSS-REFERENCE TO RELATED APPLICATIONS

This application is a continuation of U.S. patent application Ser. No. 12/327,347, filed Dec. 3, 2008, which claims the benefit of U.S. Provisional Application No. 60/992,995, filed Dec. 6, 2007, which application is incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having acetylxylan esterase activity and isolated polynucleotides encoding the polypeptides. The invention also relates to nucleic acid constructs, vectors, and host cells comprising the polynucleotides as well as methods of producing and using the polypeptides.

2. Description of the Related Art

Plant cell wall polysaccharides constitute generally 90% of the plant cell wall and can be divided into three groups: cellulose, hemicellulose, and pectin. Cellulose represents the major constituent of cell wall polysaccharides. Hemicelluloses are the second most abundant constituent of plant cell walls. The major hemicellulose polymer is xylan. The structure of xylans found in cell walls of plants can differ significantly depending on their origin, but they always contain a beta-1,4-linked D-xylose backbone. The beta-1,4-linked D-xylose backbone can be substituted by various side groups, such as L-aribinose, D-galactose, acetyl, feruloyl, p-coumaroyl, and glucuronic acid residues.

The biodegradation of the xylan backbone depends on two classes of enzymes: endoxylanases and beta-xylosidases. Endoxylanases (EC 3.2.1.8) cleave the xylan backbone into smaller oligosaccharides, which can be further degraded to xylose by beta-xylosidases (EC 3.2.1.37). Other enzymes involved in the degradation of xylan include, for example, acetylxylan esterase, arabinase, alpha-glucuronidase, feruloyl esterase, and p-coumaric acid esterase.

Acetylxylan esterase (EC 3.1.1.6) removes the 0-acetyl groups from positions 2 and/or 3 on the beta-D-xylopyranosyl residues of acetylxylan. Acetylxylan plays an important role in the hydrolysis of xylan because the acetyl side groups can interfere sterically with the approach of enzymes that cleave the backbone. Removal of the acetyl side groups facilitates the action of endoxylanases. A classification system for carbohydrate esterases, based on sequence similarity, has led to the definition of 13 families, seven of which contain acetylxylan esterases (Henrissat B., 1991, *Biochem. J.* 280: 309-316, and Henrissat and Bairoch, 1996, *Biochem. J.* 316: 695-696).

Margolles-Clark et al., 1996, *Eur. J. Biochem.* 237: 553-560, disclose an acetylxylan esterase from *Trichoderma reesei*. Sundberg and Poutanen, 1991, *Biotechnol. Appl. Biochem.* 13: 1-11, disclose the purification and properties of two acetylxylan esterases of *Trichoderma reesei*. WO 2005/001036 discloses an acetylxylan esterase gene from *Trichoderma reesei*. U.S. Pat. No. 5,681,732 discloses an acetylxylan esterase gene from *Aspergillus niger*. U.S. Pat. No. 5,763,260 discloses methods for altering the properties of acetylated xylan.

The present invention relates to polypeptides having acetylxylan esterase activity and polynucleotides encoding the polypeptides.

SUMMARY OF THE INVENTION

The present invention relates to isolated polypeptides having acetylxylan esterase activity selected from the group consisting of:

(a) a polypeptide comprising an amino acid sequence having at least 75% identity to the mature polypeptide of SEQ ID NO: 2;

(b) a polypeptide encoded by a polynucleotide that hybridizes under at least medium-high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polypeptide encoded by a polynucleotide comprising a nucleotide sequence having at least 75% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having acetylxylan esterase activity, selected from the group consisting of:

(a) a polynucleotide encoding a polypeptide comprising an amino acid sequence having at least 75% identity to the mature polypeptide of SEQ ID NO: 2;

(b) a polynucleotide that hybridizes under at least medium-high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polynucleotide comprising a nucleotide sequence having at least 75% identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having acetylxylan esterase activity.

The present invention also relates to methods of inhibiting the expression of a polypeptide having acetylxylan esterase activity in a cell, comprising administering to the cell or expressing in the cell a double-stranded RNA (dsRNA) molecule, wherein the dsRNA comprises a subsequence of a polynucleotide of the present invention. The present also relates to a double-stranded inhibitory RNA (dsRNA) molecule, wherein optionally the dsRNA is a siRNA or a miRNA molecule.

The present invention also relates to methods for degrading a xylan-containing material with a polypeptide having acetylxylan esterase activity.

The present invention also relates to plants comprising an isolated polynucleotide encoding a polypeptide having acetylxylan esterase activity.

The present invention also relates to methods of producing a polypeptide having acetylxylan esterase, comprising: (a) cultivating a transgenic plant or a plant cell comprising a polynucleotide encoding the polypeptide having acetylxylan esterase activity under conditions conducive for production of the polypeptide; and (b) recovering the polypeptide.

The present invention further relates to nucleic acid constructs comprising a gene encoding a protein, wherein the gene is operably linked to a nucleotide sequence encoding a signal peptide comprising or consisting of amino acids 1 to 19 of SEQ ID NO: 2, wherein the gene is foreign to the nucleotide sequence.

BRIEF DESCRIPTION OF THE FIGURES

FIGS. 1A and 1B show the genomic DNA sequence and the deduced amino acid sequence of a *Humicola insolens* DSM 1800 CE1 acetylxylan esterase (SEQ ID NOs: 1 and 2, respectively). Predicted intronic sequences are underlined in bold.

DEFINITIONS

Figure 2:
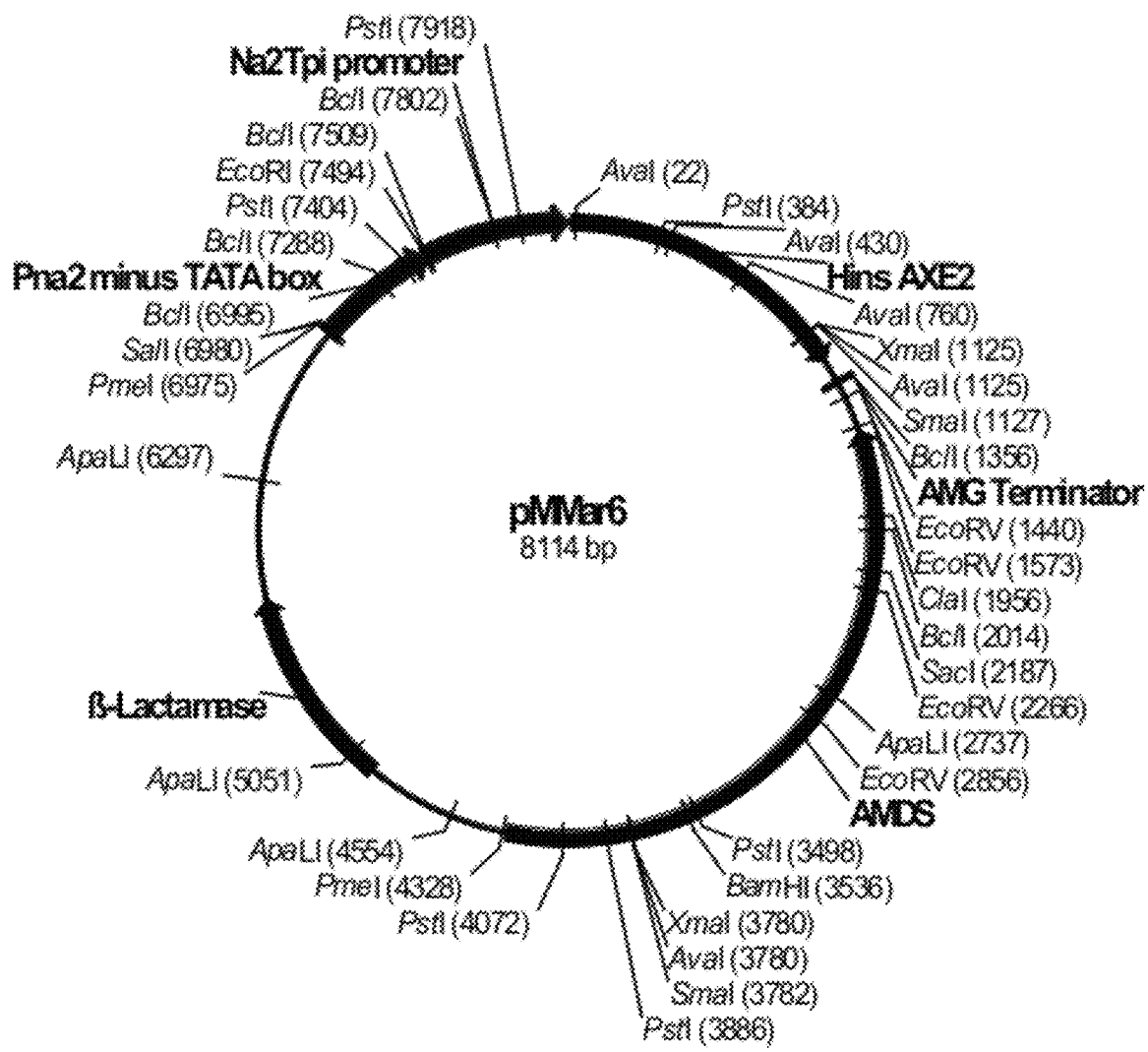
FIG. 2 shows a restriction map of pMMar6.

Acetylxylan esterase activity: The term "acetylxylan esterase activity" is defined herein as a carboxylesterase activity (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined according to the procedure described herein in the Examples. One unit of acetylxylan esterase activity is defined as the amount of enzyme capable of releasing 1 μmole of p-nitrophenolate anion per minute at pH 5, 25° C.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the acetylxylan esterase activity of the mature polypeptide of SEQ ID NO: 2.

Family CE1 or CE1: The term "Family CE1" or "CE1" is defined herein as a polypeptide falling into the carbohydrate esterase Family according to Coutinho and Henrissat, (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12.

Xylan-containing material: The term "xylan-containing material" is defined herein as any material comprising xylan as a constituent. Xylan is a plant cell wall polysaccharide containing a backbone of beta-1,4-linked xylose residues. Side chains of 4-O-methylglucuronic acid and arabinose are generally present in varying amounts, together with acetyl and feruloyl groups. Xylan is a major constituent of hemicellulose.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having acetylxylan esterase activity in its final form following translation and any post-translational modifications, such as N-terminal processing, C-terminal truncation, glycosylation, phosphorylation, etc. In a preferred aspect, the mature polypeptide is amino acids 20 to 377 of SEQ ID NO: 2 based on the SignalP program (Nielsen et al., 1997, *Protein Engineering* 10: 1-6) that predicts amino acids 1 to 19 of SEQ ID NO: 2 are a signal peptide.

Mature polypeptide coding sequence: The term "mature polypeptide coding sequence" is defined herein as a nucleotide sequence that encodes a mature polypeptide having acetylxylan esterase activity. In a preferred aspect, the mature polypeptide coding sequence is nucleotides 58 to 1266 of SEQ ID NO: 1 based on the SignalP program (Nielsen et al., 1997, supra) that predicts nucleotides 1 to 57 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that has an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Humicola insolens* acetylxylan esterase of SEQ ID NO: 2 or the mature polypeptide thereof.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has acetylxylan esterase activity. In a preferred aspect, a fragment contains at least 310 amino acid residues, more preferably at least 325 amino acid residues, and most preferably at least 340 amino acid residues, of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having acetylxylan esterase activity. In a preferred aspect, a subsequence contains at least 930 nucleotides, more preferably at least 975 nucleotides, and most preferably at least 1020 nucleotides of the mature polypeptide coding sequence of SEQ ID NO: 1 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion, and/or an insertion of one or more (several) amino acids as well as replacements of one or more (several) amino acid side chains.

Artificial variant: When used herein, the term "artificial variant" means a polypeptide having acetylxylan esterase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides having Acetylxylan Esterase Activity

In a first aspect, the present invention relates to isolated polypeptides comprising an amino acid sequence having a degree of identity to the mature polypeptide of SEQ ID NO: 2 of preferably at least 75%, more preferably at least 80%, more preferably at least 85%, even more preferably at least 90%, most preferably at least 95%, and even most preferably at least 96%, at least 97%, at least 98%, or at least 99%, which have acetylxylan esterase activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having acetylxylan esterase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 377 of SEQ ID NO: 2, or an allelic variant thereof; or a fragment thereof having acetylxylan esterase activity. In another preferred aspect, the polypeptide comprises amino acids 20 to 377 of SEQ ID NO: 2. In another preferred aspect, the polypeptide consists of the amino acid sequence of SEQ ID NO: 2 or an allelic variant thereof; or a fragment thereof having acetylxylan esterase activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 377 of SEQ ID NO: 2 or an allelic variant thereof; or a fragment thereof having acetylxylan esterase activity. In another preferred aspect, the polypeptide consists of amino acids 20 to 377 of SEQ ID NO: 2.

In a second aspect, the present invention relates to isolated polypeptides having acetylxylan esterase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having acetylxylan esterase activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having acetylxylan esterase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having acetylxylan esterase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the cDNA sequence contained in the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 58 to 1266 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pHinsAXE2 which is contained in E. coli NRRL B-50076, wherein the polynucleotide sequence thereof encodes a polypeptide having acetylxylan esterase activity. In another preferred aspect, the nucleic acid probe is the mature polypeptide coding region contained in plasmid pHinsAXE2 which is contained in E. coli NRRL B-50076.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having acetylxylan esterase activity encoded by polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which encode a polypeptide having acetylxylan esterase activity. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., acetylxylan esterase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 20 to 377 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides having Acetylxylan Esterase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having acetylxylan esterase activity of the present invention may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having acetylxylan esterase activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having acetylxylan esterase activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having acetylxylan esterase activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having acetylxylan esterase activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having acetylxylan esterase activity.

A polypeptide having acetylxylan esterase activity of the present invention may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having acetylxylan esterase activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having acetylxylan esterase activity.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having acetylxylan esterase activity.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Irpex lacteus*, *Mucor miehei*, *Myceliophthora thermophila*, *Neurospora crassa*, *Penicillium funiculosum*, *Penicillium purpurogenum*, *Phanerochaete chtysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide having acetylxylan esterase activity.

In another preferred aspect, the polypeptide is a *Humicola grisea*, *Humicola insolens*, or *Humicola lanuginosa* polypeptide having acetylxylan esterase activity.

In a more preferred aspect, the polypeptide is a *Humicola insolens* polypeptide having acetylxylan esterase activity. In a most preferred aspect, the polypeptide is a *Humicola insolens* DSM 1800 polypeptide having acetylxylan esterase activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having acetylxylan esterase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having acetylxylan esterase activity of the present invention.

In a preferred aspect, the nucleotide sequence comprises or consists of SEQ ID NO: 1. In another more preferred aspect, the nucleotide sequence comprises or consists of the sequence contained in plasmid pHinsAXE2 which is contained in *E. coli* NRRL B-50076. In another preferred aspect, the nucleotide sequence comprises or consists of the mature polypeptide coding sequence of SEQ ID NO: 1. In another preferred aspect, the nucleotide sequence comprises or consists of nucleotides 58 to 1266 of SEQ ID NO: 1. In another more preferred aspect, the nucleotide sequence comprises or consists of the mature polypeptide coding sequence contained in plasmid pHinsAXE2 which is contained in *E. coli* NRRL B-50076. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have acetylxylan esterase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Humicola*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 75%, more preferably at least 80%, more preferably at least 85%, even more preferably at least 90%, most preferably at least 95%, and even most preferably at least 96%, at least 97%, at least 98%, or at least 99% identity, which encode a polypeptide having acetylxylan esterase activity.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for acetylxylan esterase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); and (b) isolating the hybridizing polynucleotide, which encodes a polypeptide having acetylxylan esterase activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus NCIB* 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 19 of SEQ ID NO: 2. In another preferred aspect, the signal peptide coding sequence comprises or consists of nucleotides 1 to 57 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for Bacillus subtilis alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus,* and *Oceanobacillus*. Gram negative bacteria include, but not limited to, *E. coli,*

*Pseudomonas, Salmonella, Campylobacter, Helicobacter, Flavobacterium, Fusobacterium, Ilyobacter, Neisseria,* and *Ureaplasma.*

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis,* and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus,* and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol. (Praha)* 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum,*

*Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Humicola*. In a more preferred aspect, the cell is *Humicola insolens*. In a most preferred aspect, the cell is *Humicola insolens* DSM 1800.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having acetylxylan esterase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having acetylxylan esterase activity of the present invention under conditions conducive for production of the polypeptide; and (b) recovering the polypeptide.

Removal or Reduction of Acetylxylan Esterase Activity

The present invention also relates to methods of producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of acetylxylan esterase activity by fermentation of a cell that produces both a polypeptide of the present invention as well as the protein product of interest by adding an effective amount of an agent capable of inhibiting acetylxylan esterase activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of acetylxylan esterase activity by cultivating the cell under conditions permitting the expression of the product, subjecting the resultant culture broth to a combined pH and temperature treatment so as to reduce the acetylxylan esterase activity substantially, and recovering the product from the culture broth. Alternatively, the combined pH and temperature treatment may be performed on an enzyme preparation recovered from the culture broth. The combined pH and temperature treatment may optionally be used in combination with a treatment with an acetylxylan esterase inhibitor.

In accordance with this aspect of the invention, it is possible to remove at least 60%, preferably at least 75%, more preferably at least 85%, still more preferably at least 95%, and most preferably at least 99% of the acetylxylan esterase activity. Complete removal of acetylxylan esterase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially acetylxylan esterase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The acetylxylan esterase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from acetylxylan esterase activity that is produced by a method of the present invention.

Methods of Inhibiting Expression of a Polypeptide having Acetylxylan Esterase Activity The present invention also relates to methods of inhibiting the expression of a polypeptide of the present invention in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing therapeutics. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

Compositions

The present invention also relates to compositions comprising a polypeptide of the present invention. Preferably, the compositions are enriched in such a polypeptide. The term "enriched" indicates that the acetylxylan esterase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, or *Aspergillus oryzae*; *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sulphureum*, *Fusarium toruloseum*, *Fusarium trichothecioides*, or *Fusarium venenatum*; *Humicola*, preferably *Humicola insolens* or *Humicola lanuginosa*; or *Trichoderma*, preferably *Trichoderma harzianum*, *Trichoderma koningii*, *Trichoderma longibrachiatum*, *Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having acetylxylan esterase activity.

The polypeptides of the present invention can be used for degradation or modification of plant cell walls or any xylan-containing material originating from plant cells walls. Examples of various uses are described below (see, WO 2002/18561, for other uses). The dosage of the polypeptides of the present invention and other conditions under which the preparation is used may be determined on the basis of methods known in the art.

The enzymatic degradation of xylan is facilitated by full or partial removal of the side branches. The polypeptides of the present invention are preferably used in conjunction with other xylan degrading enzymes such as xylanases, acetylxylan esterases, arabinofuranosidases, xylosidases, feruloyl esterases, glucuronidases, and a combination thereof, in processes wherein xylan is to be degraded. For example, acetyl groups can be removed by acetylxylan esterases; arabinose groups by alpha-arabinosidases; feruloyl groups by feruloyl esterases, and glucuronic acid groups by alpha-glucuronidases. The oligomers released by the xylanases, or by a combination of xylanases and side branch-hydrolyzing enzymes, can be further degraded to free xylose by beta-xylosidases. A polypeptide of the present invention is preferably a component of a composition comprising one or more (several) xylan degrading enzymes, in particular xylanase. In the various uses described below, a polypeptide of the present invention is preferably used in combination with one or more (several) xylan degrading enzymes.

Consequently, the present invention also relates to methods for degrading a xylan-containing material, comprising treating the xylan-containing material with such a polypeptide having acetylxylan esterase activity. In a preferred aspect, the xylan-containing material is further treated with a xylan degrading enzyme. The xylan degrading enzyme can be selected from the group consisting of a xylanase, an acetyxylan esterase, a feruloyl esterase, an arabinofuranosidase, a xylosidase, a glucuronidase, and a combination thereof.

The plant material may be degraded in order to improve different kinds of processing, facilitate purification or extraction of components other than the xylans, like purification of beta-glucan or beta-glucan oligomers from cereals, improve the feed value, decrease the water binding capacity, improve the degradability in waste water plants, improve the conversion of, for example, grass and corn to ensilage, etc. The polypeptides of the present invention may be used in the enzymatic hydrolysis of various plant cell wall-derived materials or waste materials, e.g., from paper production, or agricultural residues such as wheat-straw, corn cobs, corn fiber, whole corn plants, nut shells, grass, vegetable hulls, bean hulls, spent grains, sugar beet pulp, and the like. The polypeptides may also be used for modifying the viscosity of plant cell wall derived material. For instance, the polypeptides may be used to reduce the viscosity of xylan-containing material, to promote processing of viscous xylan-containing material, such as in wheat separation.

The polypeptides of the present invention may also be used with limited activity of other xylanolytic enzymes to degrade xylans for production of oligosaccharides. The oligosaccharides may be used as bulking agents, like arabinoxylan oligosaccharides released from cereal cell wall material, or of more or less purified arabinoxylans from cereals.

The polypeptides of the present invention may also be used in combination with other xylanolytic enzymes to degrade xylans to xylose and other monosaccharides (U.S. Pat. No. 5,658,765). The released xylose may be converted to other compounds.

The polypeptides of the present invention may also be used in lignocellulosic biomass degradation or conversion to fermentable sugars for the production of, for example, fuel, potable ethanol, and/or fermentation products (e.g., acids, alcohols, ketones, gases, and the like). The polypeptides are preferably used in combination with other xylan degrading enzymes and a cellulase composition (endoglucanase(s), cellobiohydrolase(s), and beta-glucosidase(s)).

The polypeptides of the present invention may be used together with other enzymes like glucanases to improve the extraction of oil from oil-rich plant material, like corn-oil from corn-embryos.

The polypeptides of the present invention may also be used in baking to improve the development, elasticity, and/or stability of dough and/or the volume, crumb structure, and/or anti-staling properties of the baked product. The polypeptides may be used for the preparation of dough or baked products prepared from any type of flour or meal (e.g., based on wheat, rye, barley, oat, or maize). The baked products produced with a polypeptide of the present invention include bread, rolls, baguettes and the like. For baking purposes a polypeptide of the present invention may be used as the only or major enzymatic activity, or may be used in combination with other enzymes such as a xylanase, a lipase, an amylase, an oxidase (e.g., glucose oxidase, peroxidase), a laccase and/or a protease.

The polypeptides of the present invention may also be used for modification of animal feed and may exert their effect either in vitro (by modifying components of the feed) or in vivo. The polypeptides may be added to animal feed compositions containing high amounts of arabinoxylans and glucuronoxylans, e.g., feed containing cereals such as barley, wheat, rye, oats, or maize. When added to feed the polypeptide will improve the in vivo break-down of plant cell wall material partly due to a reduction of intestinal viscosity (Bedford et al., 1993, Proceedings of the 1st Symposium on Enzymes in Animal Nutrition, pp. 73-77), whereby improved utilization of the plant nutrients by the animal is achieved. Thereby, the growth rate and/or feed conversion ratio (i.e., the weight of ingested feed relative to weight gain) of the animal is improved.

The polypeptides of the present invention may also be used in the paper and pulp industry, inter alia in bleaching processes to enhance the brightness of bleached pulps whereby the amount of chlorine used in the bleaching stages is reduced, and to increase the freeness of pulps in the recycled paper process (Eriksson, 1990, *Wood Science and Technology* 24: 79-101; Paice et al., 1988, *Biotechnol. and Bioeng.* 32: 235-239, and Pommier et al., 1989, *Tappi Journal* 187-191). Furthermore, the polypeptides may be used for treatment of lignocellulosic pulp so as to improve the bleachability thereof. The treatment of lignocellulosic pulp may be performed, for example, as described in U.S. Pat. No. 5,658,765, WO 93/08275, WO 91/02839, and WO 92/03608.

The polypeptides of the present invention may also be used in beer brewing, in particular to improve the filterability of wort containing, for example, barley and/or sorghum malt (WO 2002/24926). The polypeptides may be used in the same manner as pentosanases conventionally used for brewing, e.g., as described by Viëtor et al., 1993, *J. Inst. Brew.* 99: 243-248; and EP 227159. Furthermore, the polypeptides may be used for treatment of brewers spent grain, i.e., residuals from beer wort production containing barley or malted barley or other cereals, so as to improve the utilization of the residuals for, e.g., animal feed.

The polypeptides of the present invention may be used for separation of components of plant cell materials, in particular of cereal components such as wheat components. Of particular interest is the separation of wheat into gluten and starch, i.e., components of considerable commercial interest. The separation process may be performed by use of methods known in the art, conveniently a so-called batter process (or wet milling process) performed as a hydroclone or a decanter process. In the batter process, the starting material is a dilute pumpable dispersion of the plant material such as wheat to be subjected to separation. In a wheat separation process the dispersion is made normally from wheat flour and water.

The polypeptides of the invention may also be used in the preparation of fruit or vegetable juice in order to increase yield.

The polypeptides of the present invention may also be used as a component of an enzymatic scouring system for textiles.

The polypeptides of the present invention may also be used in laundry detergent applications in combination with other enzyme functionalities.

Signal Peptide

The present invention also relates to nucleic acid constructs comprising a gene encoding a protein, wherein the gene is operably linked to a nucleotide sequence encoding a signal peptide comprising or consisting of amino acids 1 to 19 of SEQ ID NO: 2, wherein the gene is foreign to the nucleotide sequence.

In a preferred aspect, the nucleotide sequence comprises or consists of nucleotides 1 to 57 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Materials

Chemicals used as buffers and substrates were commercial products of at least reagent grade.

Strains

*Humicola insolens* DSM 1800 was used as the source of a Family CE1 gene encoding a polypeptide having acetylxylan esterase activity. *Aspergillus niger* MBin120 strain (WO 2004/090155) was used for expression of the Humicola insolens gene encoding the polypeptide having acetylxylan esterase activity.

Media

PDA plates were composed per liter of 39 g of potato dextrose agar.

YP medium was composed per liter of 10 g of yeast extract and 20 g of Bacto peptone.

COVE A urea-acetamide+plates were composed per liter of 20 ml of COVE A salts solution, 220 g of sorbitol, 10 g of glucose, 10 ml of 1 M acetamide, and 30 g of Bacto agar; pH 5.2.

COVE A salts solution was composed per liter of 26 g of KCl, 26 g of $MgSO_4$, 76 g of $KH_2PO_4$, and 50 ml of COVE A trace elements solution.

COVE trace elements solution was composed per liter of 0.04 g of $Na_2B_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

M410 medium was composed per liter of 50 g of maltose, 50 g of glucose, 2 g of $MgSO_4.7H_2O$, 2 g of $KH_2PO_4$, 4 g of citric acid anhydrous powder, 8 g of yeast extract, 2 g of urea, 0.5 g of AMG trace metals solution, and 0.5 g of $CaCl_2$; pH 6.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.7H_2O$, and 3 g of citric acid.

LB medium was composed per liter of 10 g of tryptone, 5 g of yeast extract, and 5 g of NaCl.

Example 1

Identification of *Humicola insolens* Acetylxylan Esterase

Protein Fractionation of ULTRAFLO® L. A 2 ml aliquot of ULTRAFLO® L (Novozymes NS, Bagsværd, Denmark) was first buffer-exchanged into 20 mM sodium acetate pH 5 with 150 mM sodium chloride, using a HIPREP™ 26/10 Desalting Column (GE Healthcare, Piscataway, N.J., USA). The resulting buffer-exchanged material (18.5 ml) was then concentrated to 3 ml using ultrafiltration with a VIVASPIN® 20 spin column with a 3,000 Dalton molecular weight cut-off membrane (Vivascience AG, Hannover, Germany). A 2 ml aliquot of the buffer-exchanged and concentrated ULTRAFLO® L material was then fractionated by size-exclusion chromatography over a HILOAD™ 26/60 SUPERDEX™ 200 prep grade size exclusion column (GE Healthcare, Piscataway, N.J., USA) by isocratic elution with the same buffer. Fractions showing UV absorbance at 280 nm were combined into six separate pools from varying elution times, ranging from 20-40 ml total volume each. Pooled fractions were concentrated to between 1-5 ml using ultrafiltration with a VIVASPIN® 20 spin column with a 3,000 Da molecular weight cut-off membrane. Twenty μl of each concentrated pooled fraction were separated on a CRITERION™ 8-16% Tris-HCl SDS-PAGE gel (Bio-Rad Laboratories, Inc., Hercules, Calif., USA) according to the manufacturer's suggested conditions. PRECISION PLUS PROTEIN™ Standards (Bio-Rad Laboratories, Inc., Hercules, Calif., USA) were used as molecular weight markers. The gel was stained with BIO-SAFE™ Coomassie stain (Bio-Rad Laboratories, Inc., Hercules, Calif., USA), and visible bands were excised with a razor blade for protein identification analysis.

In-gel digestion of polypeptides for peptide sequencing. A MULTIPROBE® II Liquid Handling Robot (PerkinElmer Life and Analytical Sciences, Boston, Mass., USA) was used to perform the in-gel digestions. A 30 kDa protein gel band was reduced with 50 μl of 10 mM dithiothreitol (DTT) in 100 mM ammonium bicarbonate pH 8.0 for 30 minutes. Following reduction, the gel piece was alkylated with 50 μl of 55 mM iodoacetamide in 100 mM ammonium bicarbonate pH 8.0 for 20 minutes. The dried gel piece was allowed to swell in 25 μl of a trypsin digestion solution containing 6 ng of sequencing grade trypsin (Promega, Madison, Wis., USA) per μl of 50 mM ammonium bicarbonate pH 8 for 30 minutes at room temperature, followed by an 8 hour digestion at 40° C. Each of the reaction steps described above was followed by numerous washes and pre-washes with the appropriate solutions following the manufacturer's standard protocol. Fifty μl of acetonitrile was used to de-hydrate the gel piece between reactions and the gel piece was air dried between steps. Peptides were extracted twice with 1% formic acid/2% acetonitrile in HPLC grade water for 30 minutes. Peptide extraction solutions were transferred to a 96 well skirted PCR type plate (ABGene, Rochester, N.Y., USA) that had been cooled to 10-15° C. and covered with a 96-well plate lid (PerkinElmer Life and Analytical Sciences, Boston, Mass., USA) to prevent evaporation. Plates were further stored at 4° C. until mass spectrometry analysis could be performed.

Protein Identification. For de novo peptide sequencing by tandem mass spectrometry, a Q-TOFMICRO™ (Waters Micromass MS Technologies, Milford, Mass., USA), a hybrid orthogonal quadrupole time-of-flight mass spectrometer, was used for LC/MS/MS analysis. The Q-TOF MICRO™ is fully microprocessor controlled using MASSLYNX™ software version 4.1 (Waters Micromass MS Technologies, Milford, Mass., USA). The Q-TOF MICRO™ was fitted with an ULTIMATE™ capillary and nano-flow HPLC system, which was coupled with a FAMOS™ micro autosampler and a SWITCHOS™ II column switching device (LCPackings/Dionex, Sunnyvale, Calif., USA) for concentrating and desalting samples. Samples were loaded onto a guard column (300 µm ID×5 cm, PEPMAP™ C18) fitted in the injection loop and washed with 0.1% formic acid in water at 40 µl per minute for 2 minutes using a Switchos II pump. Peptides were separated on a 75 µm ID×15 cm, C18, 3 µm, 100 Å PEPMAP™ nanoflow fused capillary column (LC Packings, San Francisco, Calif., USA) at a flow rate of 175 nl/minute from a split flow of 175 µl/minute using a NAN-75 calibrator (Dionex, Sunnyvale, Calif., USA). A step elution gradient of 5% to 80% acetonitrile in 0.1% formic acid was applied over a 45 minute interval. The column eluent was monitored at 215 nm and introduced into the Q-TOF MICRO™ through an electrospray ion source fitted with the nanospray interface.

Data was acquired in survey scan mode from a mass range of m/z 400 to 1990 with switching criteria for MS to MS/MS to include an ion intensity of greater than 10.0 counts per second and charge states of +2, +3, and +4. Analysis spectra of up to 4 co-eluting species with a scan time of 1.9 seconds and inter-scan time of 0.1 seconds could be obtained. A cone voltage of 45 volts was typically used and the collision energy was programmed to be varied according to the mass and charge state of the eluting peptide and in the range of 10-60 volts. The acquired spectra were combined, smoothed, and centered in an automated fashion and a peak list generated. The peak list was searched against selected databases using PROTEINLYNX™ Global Server 2.2.05 software (Waters Micromass MS Technologies, Milford, Mass., USA) and PEAKS Studio version 4.5 (SP1) (Bioinformatic Solutions Inc., Waterloo, Ontario, Canada). Results from the PROTEINLYNX™ and PEAKS Studio searches were evaluated and un-identified proteins were analyzed further by evaluating the MS/MS spectra of each ion of interest and de novo sequence was determined by identifying the y and b ion series and matching mass differences to the appropriate amino acid.

A peptide sequence was obtained from a multiple charged peptide ion recovered from the in-gel digested 30 kDa polypeptide gel band. A doubly charged tryptic peptide ion of 514.772 m/z sequence was determined to be Asn-Ser-Tyr-Pro-Gly-Tyr-[Asp or Asn]-Gly-Arg (SEQ ID NO: 4).

Example 2

*Humicola insolens* DSM 1800 Genomic DNA Extraction

*Humicola insolens* DSM 1800 was grown on PDA plates at 45° C. to confluence. Three 4 mm² squares were cut from the PDA plates, inoculated into 25 ml of YP medium containing 2% glucose in a baffled 125 ml shake flask, and incubated at 41° C. with shaking at 200 rpm for 2 days. Mycelia were harvested by filtration using MIRACLOTH® (Calbiochem, La Jolla, Calif., USA), washed twice in deionized water, and frozen under liquid nitrogen. Frozen mycelia were ground, by mortar and pestle, to a fine powder, and total DNA was isolated using a DNEASY® Plant Maxi Kit (QIAGEN Inc., Valencia, Calif., USA).

Example 3

Isolation of a Partial Fragment of an Acetylxylan Esterase Gene from *Humicola insolens* DSM 1800

Using the Consensus-Degenerate Hybrid Oligonucleotide Primer Program (CODEHOP; Rose et al., 1998, *Nucleic Acids Research* 26: 1628-1635), degenerate primers, shown below, were designed to the identified peptide described in Example 1.

```
Primer HiFAE-degF
                                        (SEQ ID NO: 5)
5'-WSNYTNCARCARGTNTGGAAYTGGGGNGCNAAY-3'

Protein translation for degenerate primer
HiFAE-degF:
                                        (SEQ ID NO: 6)
XXQQVWNWGA Primer HiFAE-degR:
                                        (SEQ ID NO: 7)
5'-GGCGGCGGCCGTCRTANCCNGGRTA-3'

Protein translation for degenerate primer
HiFAE-degR:
YPGYDGRR
```

To obtain the initial DNA fragment of the *Humicola insolens* acetylxylan esterase gene, the amplification reaction (25 µl) was composed of 117 ng of *Humicola insolens* DSM 1800 genomic DNA as template, 0.4 mM each of dATP, dTTP, dGTP, and dCTP, 50 pmol each of primer HiFAE-degR and primer HiFAE-degF, 1× ADVANTAGE® GC-Melt LA Buffer (Clontech Laboratories, Inc., Mountain View, Calif., USA), and 1.25 units of ADVANTAGE® GC Genomic Polymerase Mix. The amplification was performed using an EPPENDORF® MASTERCYCLER® 5333 (Eppendorf Scientific, Inc., Westbury, N.Y., USA) programmed for predenaturing at 94° C. for 1 minute; 30 cycles each at a denaturing temperature of 94° C. for 30 seconds; annealing temperature of 60° C. for 30 seconds; elongation at 72° C. for 90 seconds; and final elongation at 72° C. for 5 minutes.

The reaction products were isolated by 1.0% agarose gel electrophoresis in TBE (10.8 g of Tris base, 5.5 g of boric acid and 4 ml of 0.5 M EDTA pH 8.0 per liter) buffer. A PCR product band of approximately 1.1 kb was excised from the gel, purified using a QIAQUICK® Gel Extraction Kit (QIAGEN Inc., Valencia, Calif., USA) according to the manufacturer's instructions, and sequenced. Based on the sequencing it was found that primer HiFAE-degF did not bind during the amplification, while primer HiFAE-degR bound to both ends. A partial sequence was obtained which encoded a peptide fragment that was homologous to a putative acetylxylan esterase from *Neosartorya fischeri* (Uniprot:A1DBP9).

Example 4

Identification of a Full-Length *Humicola insolens* Acetylxylan Esterase Gene

A full-length acetylxylan esterase gene was identified from *Humicola insolens* DSM 1800 using a GENOMEWALKER™ Universal Kit (Clontech Laboratories, Inc., Mountain View, Calif., USA) according to the manufacturer's instructions. Briefly, total genomic DNA from *Humicola insolens* DSM 1800 was digested separately with four different restriction enzymes (Dra I, Eco RV, Pvu II, and Stu I) that leave blunt ends. Each batch of digested genomic DNA was then ligated separately to the GENOMEWALKER™ Adaptor (Clontech Laboratories, Inc., Mountain View, Calif., USA) to create four libraries. These four libraries were then employed as templates in PCR reactions using two gene-specific primers shown below, one for a primary PCR and one for a secondary PCR amplifying downstream of the fragment through the 3' end encoding the C-terminus of the acetylxylan esterase. Based on sequence homology to other acetylxylan esterases, it appeared the 5' end encoding the N-terminus of the acetylxylan esterase was contained within the initial fragment described in Example 3. The following primers were designed based on the partial acetylxylan esterase gene sequence from *Humicola insolens* obtained as described in Example 3:

```
Primer Hins_AXE_GSP1_F1 (primary):
                                    (SEQ ID NO: 8)
5'-CTACACGGGCACTGTTGCTGGCTGGAA-3'

Primer Hins_AXE_GSP2_F3 (secondary):
                                    (SEQ ID NO: 9)
5'-ACACTGGGCCAGGACGGCGCTCGATAT-3'
```

The primary amplifications were composed of 1 µl (approximately 6 ng) of each library as template, 0.4 mM each of dATP, dTTP, dGTP, and dCTP, 10 pmol of Adaptor Primer 1 (Clontech Laboratories, Inc., Mountain View, Calif., USA), 50 pmol of primer Hins_AXE_GSP1_F1, 1× ADVANTAGE® GC-Melt LA Buffer (Clontech Laboratories, Inc., Mountain View, Calif., USA), and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 5 cycles each at a denaturing temperature of 95° C. for 25 seconds; annealing and elongation at 72° C. for 5 minutes; 7 cycles each at a denaturing temperature of 95° C. for 25 seconds; annealing and elongation at 72° C. for 5 minutes; 32 cycles each at a denaturing temperature of 95° C. for 25 seconds; annealing and elongation at 67° C. for 5 minutes; and a final elongation at 67° C. for 7 minutes.

The secondary amplifications were composed of 1 µl of each primary PCR product as template, 0.4 mM each of dATP, dTTP, dGTP, and dCTP, 10 pmol of Adaptor Primer 2 (Clontech Laboratories, Inc., Mountain View, Calif., USA), 50 pmol of primer Hins_AXE_GSP2_F3, 1× ADVANTAGE® GC-Melt LA Buffer, and 1.25 units of ADVANTAGE® GC Genomic Polymerase Mix in a final volume of 25 µl. The amplifications were performed using an EPPENDORF® MASTERCYCLER® 5333 programmed for pre-denaturing at 95° C. for 1 minute; 5 cycles each at a denaturing temperature of 95° C. for 25 seconds; annealing and elongation at 72° C. for 5 minutes; 20 cycles each at a denaturing temperature of 95° C. for 25 seconds; annealing and elongation at 67° C. for 5 minutes; and final elongation at 67° C. for 7 minutes.

The reaction products were isolated by 1.0% agarose gel electrophorsis in TBE buffer. From the Pvu II library, 1 kb and 1.8 kb products were excised from the gel, purified using a QIAQUICK® Gel Extraction Kit (QIAGEN, Valencia, Calif., USA) according to the manufacturer's instructions, and sequenced.

DNA sequencing of the PCR fragments was performed with a Perkin-Elmer Applied Biosystems Model 377 XL Automated DNA Sequencer using dye-terminator chemistry (Giesecke et al., 1992, supra) and primer walking strategy. Adaptor Primer 2 and primer Hins_AXE_GSP2_F3 were used for sequencing.

Nucleotide sequence data were scrutinized for quality and all sequences were compared to each other with assistance of PHRED/PHRAP software (University of Washington, Seattle, Wash., USA). The PCR fragment sequence results were compared and aligned with the partial acetylxylan esterase gene sequence from *Humicola insolens* described in Example 3. A gene model was constructed based on the gene fragments obtained in this Example and in Example 3 allowing determination of the 5' and 3' ends of the gene with other homologous acetylxylan esterases.

Example 5

Cloning of the *Humicola insolens* Acetylxylan Esterase Gene and Construction of an *Aspergillus niger* Expression Vector Two synthetic oligonucleotide primers shown below were designed to PCR amplify the *Humicola insolens* acetylxylan esterase gene from the genomic DNA prepared in Example 2. An InFusion Cloning Kit (BD Biosciences, Palo Alto, Calif., USA) was used to clone the fragment directly into the expression vector pBM120a (WO 2006/078256).

```
HinsAXEBDinfnterm:
                                    (SEQ ID NO: 10)
5'-ACACAACTGGCCATGAAGGTCCCGACTCTCATCTCG-3'

HinsAXEBDinfCtermendPacI:
                                    (SEQ ID NO: 11)
5'-CAGTCACCTCTAGTTATTACAGGCACTGAGAGTACC-3'
```

Bold letters represent coding sequence. The remaining sequence is homologous to the insertion sites of pBM120a.

Fifty picomoles of each of the primers above were used in a PCR reaction composed of 80 ng of *Humicola insolens* genomic DNA, 1× ADVANTAGE® GC-Melt LA Buffer, 0.4 mM each of dATP, dTTP, dGTP, and dCTP, and 1.25 units of ADVANTAGE® GC Genomic Polymerase Mix in a final volume of 25 µl. The amplification was performed using an EPPENDORF® MASTERCYCLER® 5333 programmed for 1 cycle at 94° C. for 1 minute; 30 cycles each at 94° C. for 30 seconds, 58° C. for 30 seconds, and 72° C. for 90 seconds; and a final elongation at 70° C. for 5 minutes. The heat block then went to a 4° C. soak cycle.

The reaction products were isolated by 1.0% agarose gel electrophoresis in TBE buffer where an approximately 1.2-1.3 kb product band was excised from the gel, and purified using a QIAQUICK® Gel Extraction Kit according to the manufacturer's instructions.

Plasmid pBM120a was digested with Nco I and Pac I, isolated by 1.0% agarose gel electrophoresis in TBE buffer, and purified using a QIAQUICK® Gel Extraction Kit according to the manufacturer's instructions.

The gene fragment and the digested vector were ligated together using an InFusion Cloning Kit resulting in pMMar6 (FIG. 2) in which transcription of the acetylxylan esterase gene was under the control of a hybrid of promoters from the genes for *Aspergillus niger* neutral alpha-amylase and *Aspergillus oryzae* triose phosphate isomerase (NA2-tpi promoter). The ligation reaction (20 µl) was composed of 1× InFusion Buffer (BD Biosciences, Palo Alto, Calif., USA), 1× BSA (BD Biosciences, Palo Alto, Calif., USA), 1 µl of InFusion enzyme (diluted 1:10) (BD Biosciences, Palo Alto, Calif., USA), 106 ng of pBM120a digested with Nco I and Pac I, and 208 ng of the purified *Humicola insolens* acetylxylan esterase PCR product. The reaction was incubated at room temperature for 30 minutes. Two µl of the reaction was used to transform *E. coli* XL10 SOLOPACK® Gold Supercompetent cells (Stratagene, La Jolla, Calif., USA) according to the manufacturer's instructions. An *E. coli* transformant containing pMMar6 was detected by restriction digestion and plasmid DNA was prepared using a BIOROBOT® 9600 (QIAGEN Inc., Valencia, Calif., USA). The *Humicola insolens* acetylxylan esterase gene insert in pMMar6 was confirmed by DNA sequencing with a Perkin-Elmer Applied Biosystems Model 377 XL Automated DNA Sequencer using dye-terminator chemistry (Giesecke et al., 1992, supra) and primer walking strategy. Primer 996271 Na2tpi promoter fwd and primer 996270 AMG rev, shown below, were used for sequencing.

```
996271 Na2tpi promoter fwd:
                                      (SEQ. ID NO: 12)
5'-ACTCAATTTACCTCTATCCACACTT-3'

996270 AMG rev:
                                      (SEQ. ID NO: 13)
5'-CTATAGCGAAATGGATTGATTGTCT-3'
```

Figure 3:
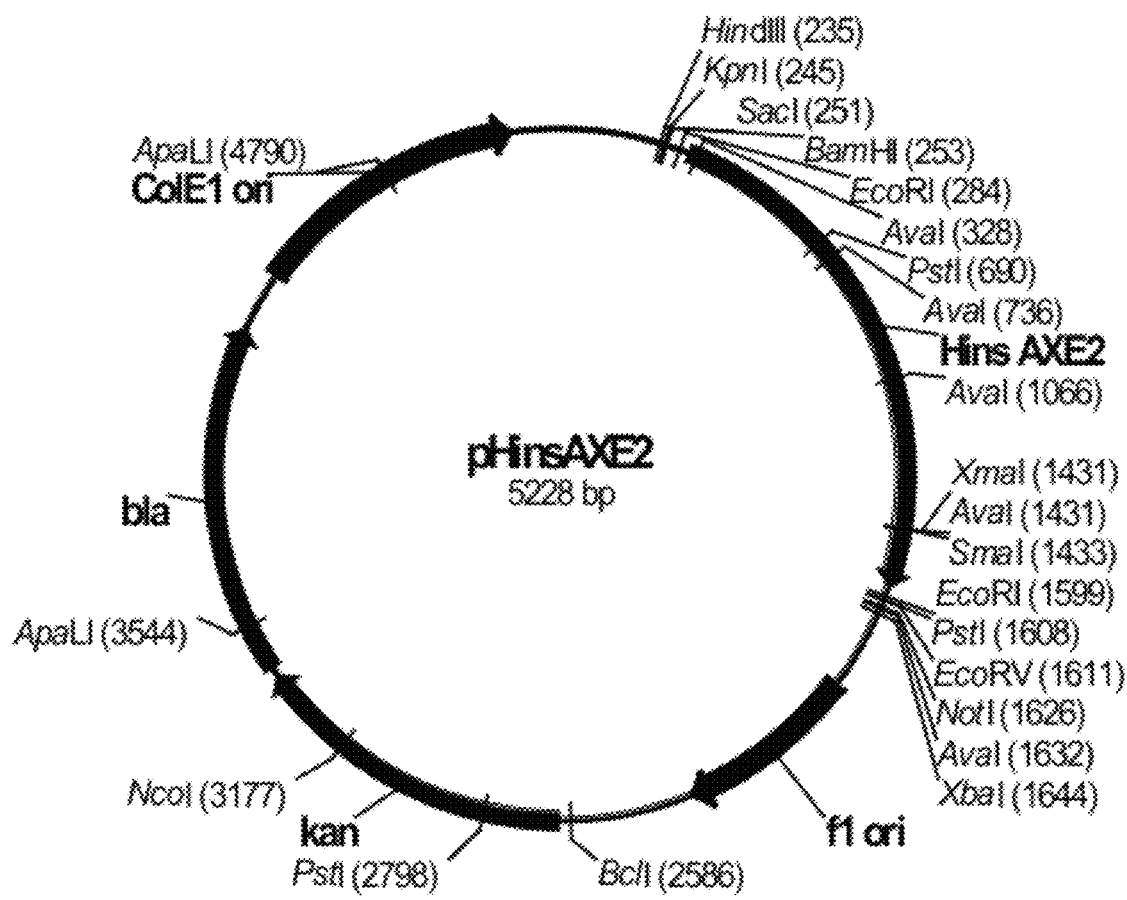
FIG. 3 shows a restriction map of pHinsAXE2.

A clone containing pMMar6 was picked into 2×50 ml of LB medium containing 100 µg of ampicillin per ml and grown overnight in 250 ml glass flasks at 37° C. with shaking at 200 rpm. Plasmid pMMar6 was isolated using a QIAGEN® Midi Kit according to the manufacturer's instructions. Plasmid pMMar6 was digested with Pme I, isolated by 1.0% agarose gel electrophoresis in TBE buffer, and the fragment containing the acetylxylan esterase gene was purified using a QIAQUICK® Gel Extraction Kit according to the manufacturer's instructions in preparation for transforming *Aspergillus niger* MBin120 protoplasts. The same approximately 1.2-1.3 kb PCR fragment was cloned into pCR® 2.1-TOPO® vector (Invitrogen, Carlsbad, Calif., USA) using a TOPO® TA CLONING Kit (Invitrogen, Carlsbad, Calif., USA), to generate pHinsAXE2 (FIG. 3). The *Humicola insolens* acetylxylan esterase gene insert in pHinsAXE2 was confirmed by DNA sequencing. *E. coli* pHinsAXE2 was deposited with the Agricultural Research Service Patent Culture Collection, Northern Regional Research Center, Peoria, Ill., USA, on Nov. 20, 2007.

Example 6

Characterization of the *Humicola insolens* Genomic Sequence Encoding a Family CE1 Acetylxylan Esterase (AXE2)

Nucleotide sequence data (Example 5) were scrutinized for quality and all sequences were compared to each other with assistance of PHRED/PHRAP software (University of Washington, Seattle, Wash., USA).

Figure 1A:
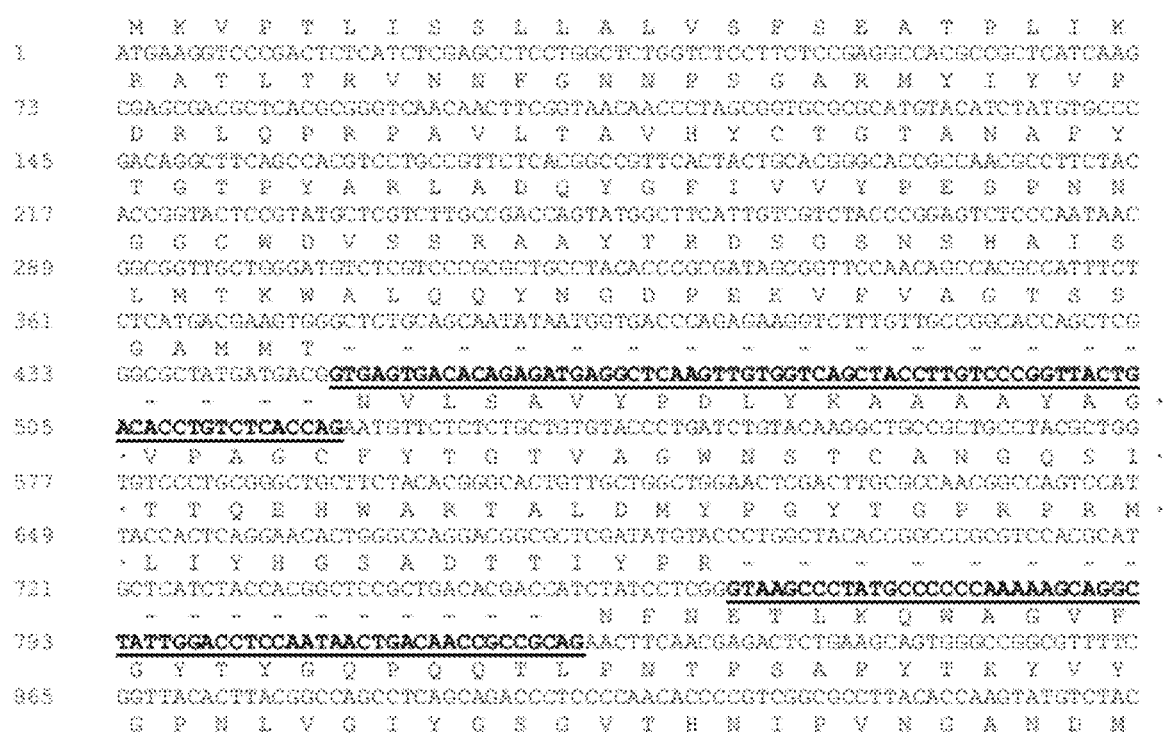

The nucleotide sequence (SEQ ID NO: 1) and deduced amino acid sequence (SEQ ID NO: 2) are shown in FIGS. 1A and 1B. The genomic fragment encodes a polypeptide of 377 amino acids, interrupted by 2 predicted introns of 73 by and 62 bp. The % G+C content of the full-length coding sequence and the mature coding sequence are 60.4% and 60.5%, respectively. Using the SignalP software program (Nielsen et al., 1997, *Protein Engineering* 10: 1-6), a signal peptide of 19 residues was predicted. The predicted mature protein contains 358 amino acids with a molecular mass of 38.5 kDa. A predicted esterase polyhydroxybutyrate depolymerase domain occurs at amino acids 43 to 257 and a predicted cellulose-binding domain at amino acids 341 to 377. Based on the deduced amino acid sequence, the acetylxylan esterase appears to fall into the carbohydrate esterase Family CE1 according to Coutinho and Henrissat, 1999, supra.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the mature polypeptide of the *Humicola insolens* Family CE1 acetylxylan esterase gene shared 72.4% identity (excluding gaps) to the deduced amino acid sequence of a *Chaetomium gracile* acetylxylan esterase (GeneSeqP accession number AAB82124).

Example 7

Transformation and Expression of the *Humicola insolens* Family CE1 Acetylxylan Esterase Gene in *Aspergillus niger* MBin120

The *Humicola insolens* Family CE1 acetylxylan esterase gene was expressed in *Aspergillus niger* MBin120. *Aspergillus niger* MBin120 protoplasts were prepared according to the method of Christensen et al., 1988, *Bio/Technology* 6: 1419-1422. Five µg of Pme I digested pMMar6 were used to transform *Aspergillus niger* MBin120.

The transformation of *Aspergillus niger* MBin120 with the Pme I digested pMMar6 yielded approximately 45 transformants. Twenty-five transformants were isolated to individual COVE A urea-acetamide+plates. Two 3 mm square agar plugs were cut from the confluent COVE A urea-acetamide+ plates of the 25 transformants and inoculated separately into 25 ml of M410 medium in 125 ml plastic shake flasks and incubated at 34° C. with shaking at 250 rpm. After 5 days incubation, 6 µl of supernatant from each culture were analyzed on a CRITERION™ 8-16% Tris-HCl SDS-PAGE gel with a CRITERION® Cell (Bio-Rad Laboratories, Inc., Hercules, Calif., USA), according to the manufacturer's instructions. The resulting gel was stained with BIO-SAFE™ Coomassie stain.

SDS-PAGE profiles of the cultures showed that approximately half of the transformants had a major band of approximately 50 kDa. One transformant designated *Aspergillus niger* MMar204 was chosen for expression of the *Humicola insolens* polypeptide having acetylxylan esterase activity in *Aspergillus niger*.

Example 8

Fermentation of *Aspergillus niger* MMar204

Shake flask medium was composed per liter of 70 g of sucrose and 100 g of soy concentrate. Trace metals solution was composed per liter of 13.8 g of $FeSO_4.7H_2O$, 14.3 g of $ZnSO_4.7H_2O$, 11.6 g of $MnSO_4.H_2O$, 2.5 g of $CuSO_4.5H_2O$, 0.5 g of $NiCl_2.6H_2O$ and 3.3 g of citric acid monohydrate.

One hundred ml of shake flask medium were added to each of four 500 ml shake flasks. The shake flasks were each inoculated with 200 µl from a glycerol spore stock of *Aspergillus niger* MMar204 and incubated at 30° C. on an orbital shaker at 220 rpm for 72 hours. Fifty ml of the shake flask broth from each of the four shake flasks were used to inoculate a 3 liter fermentation vessel.

Fermentation batch medium was composed per liter of 250 g of glucose, 5 g of $(NH_4)_2SO_4$, 2.5 g of $KH_2PO_4$, 0.5 g of $CaCl_2.2H_2O$, 2 g of $MgSO_4.7H_2O$, 3 g of $K_2SO_4$, 1 g of citric acid, 1 ml of anti-foam, and 0.75 ml of trace metals solution. The trace metals solution was composed per liter of 13.8 g of $FeSO_4.7H_2O$, 14.3 g of $ZnSO_4.7H_2O$, 11.6 g of $MnSO_4.H_2O$, 2.5 g of $CuSO_4.5H_2O$, 0.5 g of $NiCl_2.6H_2O$, and 3.3 g of citric acid monohydrate. Fermentation feed medium was composed per kilogram of 406 g of maltose, 0.5 g of citric acid monohydrate, and 1 ml of anti-foam.

A total of 2 liters of the fermentation batch medium was added to an Applikon Biotechnology two liter glass jacketed fermentor (Applikon Biotechnology, Schiedam, Netherlands). Fermentation feed medium was dosed at a rate of 0 to 4 g/l/hr for a period of 185 hours. The fermentation vessel was maintained at a temperature of 34° C. and pH was controlled using an Applikon 1030 control system (Applikon Biotechnology, Schiedam, Netherlands) to a set-point of 5.1+/−0.1. Air was added to the vessel at a rate of 1 vvm and the broth was agitated by Rushton impeller rotating at 1100 rpm. At the end of the fermentation, whole broth was harvested from the vessel and centrifuged at 3000×g to remove the biomass. The supernatant was sterile filtered and stored at 5 to 10° C.

Example 9

Purification of the *Humicola insolens* Acetylxylan Esterase (AXE2)

Supernatant of the fermentation broth described in Example 8 was first buffer-exchanged into 20 mM MES pH 6 and concentrated using a Pall Filtron tangential flow filtration system consisting of an Ultrapump II, an ULTRARESERVOIR™ 5L, and an ULTRASETTE™ 10K Omega tangential flow filtration membrane with a 10,000 Da molecular weight cut-off (Pall Corporation, East Hills, N.Y., USA). The resulting buffer-exchanged material (150 ml) was then purified over 120 ml of SP SEPHAROSE™ Big Beads resin (GE Healthcare, Piscataway, N.J., USA) equilibrated with 20 mM MES pH 6, and then eluted with a linear gradient of 0-1 M sodium chloride. Fractions were collected and monitored at 280 nm. A 2.5 µl aliquot of the fractions having UV absorbance at 280 nm were analyzed on a CRITERION™ 8-16% Tris-HCl SDS-PAGE gel according to the manufacturer's suggested conditions. PRECISION PLUS PROTEIN™ Standards were used as molecular weight markers. The gel was stained with BIO-SAFE™ Coomassie stain. Fractions showing a band at 55 kDa, corresponding to the *Humicola insolens* acetylxylan esterase, were combined to yield purified acetylxylan esterase (130 ml) of greater than 90% purity.

The *Humicola insolens* acetylxylan esterase was assayed for enzyme activity using p-nitrophenylacetate as substrate (Sigma-Aldrich Chemical co., Inc., St Louis, Mo., USA). Activity assays were performed in a 96-well COSTAR® microtiter plate (Corning Inc., Corning, N.Y., USA). A 100 mM p-nitrophenylacetate solution was initially prepared in DMSO, and then diluted to a 1 mM solution in 50 mM sodium acetate pH 5.0 with 0.01% TWEEN® 20. The enzyme reaction was then initiated by adding an aliquot of the purified *Humicola insolens* acetylxylan esterase to the 1 mM p-nitrophenylacetate suspension, resulting in a final substrate concentration of 0.5 mM p-nitrophenylacetate. The reaction was allowed to proceed for 10 minutes at ambient temperature (25° C.), at which time 1 M Tris-HCl pH 8.0 was added, and the amount of p-nitrophenolate anion released was determined by an increase in absorbance at 405 nm using a SPECTRAMAX™ 340 PC plate reader (Molecular Devices, Sunnyvale, Calif., USA). Protein concentration of the purified was determined using a Microplate BCA™ Protein Assay Kit (Pierce, Rockford, Ill., USA). One unit of acetylxylan esterase activity is defined as the amount of enzyme capable of releasing 1 µmole of p-nitrophenolate anion per minute at pH 5, 25° C.

The *Humicola insolens* acetylxylan esterase was determined to have an activity of 15.4 units per mg of enzyme.

Example 10

Thermostability of *Humicola insolens* Acetylxylan Esterase

The thermostability of the purified *Humicola insolens* polypeptide having acetylxylan esterase activity (Example 9) was determined by differential scanning calorimetry (DSC) using a A VP-DSC (MicroCal Inc., Northampton, Mass., USA) according to the manufacturer's instructions in 50 mM sodium acetate pH 5.0.

The thermal denaturation temperature, Td, was taken as the top of the denaturation peak (major endothermic peak) in a thermogram (Cp vs. T) obtained after heating of the enzyme solution at a programmed heating rate of 90° C. per hour beginning at 20° C. The Td for the acetylxylan esterase under these conditions was 71(+/−1)° C.

Example 11

Effect of *Humicola insolens* Acetylxylan Esterase on Hydrolysis of Pretreated Corn Fiber The effect of *Humicola insolens* acetylxylan esterase on hydrolysis of pretreated corn fiber was evaluated. Corn fiber is a fraction from the wet milling of corn kernels. Corn fiber is the seed coat and residual endosperm left after starch is removed and further processed. Corn fiber was pretreated by autoclaving at 140° C. for 150 minutes. The amount of arabinose, glucose and xylose in the substrate was determined to be 175, 317, and 261 g per kg dry matter.

Arabinose and xylose were determined by carbohydrate hydrolysis using dilute hydrochloric acid. The pretreated corn fiber was transferred to 125 ml conical flasks and diluted to contain approximately 10% dry matter. The corn fiber sample was preheated at 100° C. in an oil bath. Hydrolysis was started by adding 5 ml of 2 M hydrochloric acid for 2 hours at 100° C. After incubation the flasks were cooled on ice and neutralized with 4 M sodium hydroxide. Samples were filtered with a MINISART® 0.2 micron syringe filter (Sartorius AG, Goettingen, Germany) and analyzed for arabinose and xylose on a DIONEX BIOLC® System (Dionex Corporation, Sunnyvale, Calif., USA). Glucose was determined by subjecting the pretreated sample of corn fiber to a two step sulfuric acid hydrolysis. Three ml of 72% sulfuric acid was added to approximately 300 mg of dried corn fiber in pressure tubes (Ace Glass, Inc., Vineland, N.J., USA). Samples were mixed and placed in a water bath at 30° C. for 60 minutes. Samples were stirred every 5 to 10 minutes. After 60 minutes the samples were removed and 84 ml of deionized water was added. Samples were placed in an autoclave and heated for 1 hour at 121° C. After cooling the samples were filtered to remove remaining solids and neutralized by addition of calcium carbonate.

Glucose concentration was determined with a DIONEX® BIOLC® System according to the following method.

Samples (10 µl) were loaded onto a DIONEX BIOLC® System equipped with a DIONEX® CARBOPAC™ PA1 analytical column (4×250 mm) (Dionex Corporation, Sunnyvale, Calif., USA) combined with a CARBOPAC™ PA1 guard column (4×50 mm) (Dionex Corporation, Sunnyvale, Calif., USA). The monosaccharides were separated isocratically with 10 mM potassium hydroxide at a flow rate of 1 ml per minute and detected by a pulsed electrochemical detector in the pulsed amperiometric detection mode. The potential of the electrode was programmed for +0.1 volt (t=0-0.4 second) to −2.0 volt (t=0.41-0.42 second) to 0.6 volt (t=0.43 second) and finally −0.1 volt (t=0.44-0.50 second), while integrating the resulting signal from t=0.2-0.4 second. A mixture of arabinose, galactose, glucose, and xylose (concentration of each component: 0.0050-0.075 g per liter) was used as standard.

The hydrolysis of the pretreated corn fiber was conducted with a *Trichoderma reesei* cellulolytic protein composition (*Trichoderma reesei* broth comprising *Thermoascus aurantiacus* GH61A polypeptide having cellulolytic enhancing activity and *Aspergillus oryzae* beta-glucosidase fusion; PCT/US2008/065417) and a Trichoderma reesei beta-xylosidase. The *Trichoderma reesei* beta-xylosidase was obtained recombinantly by expression in *Aspergillus oryzae* as described in Rasmussen et al., 2006, *Biotechnology and Bioengineering* 94: 869-876 using standard cultivation methods for *Aspergillus oryzae*. The *Humicola insolens* acetylxylan esterase was obtained as described in Example 9.

The hydrolysis of the pretreated corn fiber was performed in 2 ml EPPENDORF® tubes (Eppendorf AG, Germany) at a temperature of 50° C. and a pH of 5.0 in 50 mM succinic acid. Samples were incubated in a THERMOMIXER® Comfort (Eppendorf AG, Germany) that subjected each sample with constant heating and mixing. The substrate amount used was 2.5 w/w % in a total sample volume of 2 ml. The acetylxylan esterase from *Humicola insolens* was added at an enzyme loading of 1 mg enzyme per g of dry matter on top of both the *Trichoderma reesei* cellulolytic protein composition and the *Trichoderma reesei* beta-xylosidase. The *Trichoderma reesei* cellulolytic protein composition was added at a loading of 5 mg enzyme per g of dry matter and the *Trichoderma reesei* beta-xylosidase at a loading of 1 mg enzyme per g of dry matter. Hydrolysis was terminated after 24 hours by heating the samples for 10 minutes at 100° C. in a heat block (Techne Inc., Burlington N.J., USA).

Quantification of acetic acid was performed by high pressure liquid chromatography using two AMINEX® HPX-87H columns (Bio-Rad Laboratories, Hercules, Calif., USA) coupled in series with a pre-column (Micro-Guard Cation H Refill Cartridges, Bio-Rad Laboratories, Hercules, Calif., USA) with a WATERS® 515 Pump, WATERS® MPSA Millipore, WATERS® 717 Plus Autosampler, WATERS® Column Heater Module and WATERS® 2410 RI detector (Waters Corporation, Milford, Mass., USA). The chromatography was performed at 60° C. with a flow of 0.4 ml/minute of 0.005 M sulfuric acid.

Conversion was calculated by determining the amount of sugars released from the substrate as a percentage of what was added from the start using the formula below. T-tests were performed with a two tailed distribution and equal variance of sample data.

Conversion (%)=(Sugar amount in hydrolysate/Sugar amount in added substrate)×100

Comparing the conversion of pretreated corn fiber when adding the acetylxylan esterase from *Humicola insolens* at an enzyme loading of 1 mg of enzyme per gram dry matter together with 1 mg enzyme per g of dry matter of *Trichoderma reesei* beta-xylosidase and 5 mg enzyme per g of dry matter of *Trichoderma reesei* cellulolytic protein composition to just adding 1 mg enzyme per g of dry matter of beta-xylosidase from *Trichoderma reesei* and 5 mg enzyme per g of dry matter of *Trichoderma reesei* cellulolytic protein composition demonstrated a significant ($P \leq 0.0519$) increase in relative conversion from 100.0 to 109.9 (Table 1).

TABLE 1

| Samples | Relative total conversion | Standard deviation | T-test |
| --- | --- | --- | --- |
| *Trichoderma reesei* cellulolytic protein composition and *Trichoderma reesei* beta-xylosidase | 100.0 | 3.2 | 0.0519 |
| *Trichoderma reesei* cellulolytic protein composition, *Trichoderma reesei* beta-xylosidase, and *Humicola insolens* acetylxylan esterase | 109.9 | 3.4 | |

The release of acetic acid from the substrate increased significantly ($P \leq 0.0004$) from 100.0 to 236.0 by adding the *Humicola insolens* acetylxylan esterase to the combination of *Trichoderma reesei* cellulolytic protein composition and the *Trichoderma reesei* beta-xylosidase (Table 2).

TABLE 2

| Samples | Relative release of acetic acid | Standard deviation | T-test |
| --- | --- | --- | --- |
| *Trichoderma reesei* cellulolytic protein composition and *Trichoderma reesei* beta-xylosidase | 100.0 | 10.0 | 0.0004 |
| *Trichoderma reesei* cellulolytic protein composition, *Trichoderma reesei* beta-xylosidase, and *Humicola insolens* acetylxylan esterase | 236.0 | 2.8 | |

Example 12

Effect of *Humicola insolens* Acetylxylan Esterase on the Hydrolysis of D-Xylose Tetraacetate The effect of *Humicola insolens* acetylxylan esterase on the hydrolysis of D-xylose tetraacetate was evaluated. The *Humicola insolens* acetylxylan esterase was obtained as described in Example 9.

Hydrolysis of D-xylose tetraacetate (Benn Chemicals, Dielsdorf, Switzerland) was performed in 1.5 ml EPPENDORF® tubes at a temperature of 50° C. and a pH of 5.0 in 50 mM succinic acid for 48 hours. Samples were incubated in a THERMOMIXER® Comfort that subjected each sample with constant heating and mixing. The substrate amount used was 1 ml at a concentration of 1 w/w % of D-xylose tetraacetate. The control sample (1 ml of substrate) was compared with the *Humicola insolens* acetylxylan esterase sample (1 ml of substrate+7 µl of enzyme). The *Humicola insolens* acetylxylan esterase was added at an enzyme loading of 0.5 mg *Humicola insolens* acetylxylan esterase/g dry solids. Hydrolysis was terminated after 48 hours by heating the samples for 10 minutes at 100° C. in a heat block.

The amount of acetate was analyzed by HPLC as described in Example 11. Addition of 0.5 mg of *Humicola insolens* acetylxylan esterase to 1 ml of substrate (1 w/w % of D-xylose tetraacetate) resulted in a calculated release of 89.2 µmol/ml acetate (Table 3). The release of acetate by *Humicola insolens* acetylxylan esterase was calculated from the concentrations of the control sample (1.9 µmol/ml) and the *Humicola insolens* acetylxylan esterase sample (91.1 µmol/ml).

TABLE 3

| Samples | Concentration of acetate (μmol/ml) | Enzyme released acetate (μmol/ml) |
|---|---|---|
| Control | 1.9 | |
| *Humicola insolens* acetylxylan esterase | 91.1 | 89.2 |

Deposit of Biological Material

The following biological material has been deposited under the terms of the Budapest Treaty with the Agricultural Research Service Patent Culture Collection (NRRL), Northern Regional Research Center, Peoria, Ill., USA, and given the following accession number:

| Deposit | Accession Number | Date of Deposit |
|---|---|---|
| *E. coli* pHinsAXE2 | NRRL B-50076 | Nov. 20, 2007 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide having acetylxylan esterase activity, comprising the mature polypeptide of SEQ ID NO: 2.

2. The polypeptide of claim 1, consisting of the mature polypeptide of SEQ ID NO: 2.

3. The polypeptide of claim 1, wherein the mature polypeptide is 20 to 377 of SEQ ID NO: 2.

4. The polypeptide of claim 1, which is encoded by a polynucleotide comprising or consisting of the mature polypeptide coding sequence of SEQ ID NO: 1.

5. The polypeptide of claim 4, wherein the mature polypeptide coding sequence is nucleotides 58 to 1266 of SEQ ID NO: 1.

6. An isolated polynucleotide comprising a nucleotide sequence that encodes the polypeptide of claim 1.

7. A nucleic acid construct comprising the polynucleotide of claim 6 operably linked to one or more (several) control sequences that direct the production of the polypeptide in an expression host.

8. A recombinant host cell comprising the nucleic acid construct of claim 7.

9. A method of producing the polypeptide of claim 1, comprising: (a) cultivating a cell, which in its wild-type form produces the polypeptide, under conditions conducive for production of the polypeptide; and (b) recovering the polypeptide.

10. A method of producing the polypeptide of claim 1, comprising: (a) cultivating a host cell comprising a nucleic acid construct comprising a polynucleotide encoding the polypeptide under conditions conducive for production of the polypeptide; and (b) recovering the polypeptide.

11. A method of producing a mutant of a parent cell, comprising disrupting or deleting a nucleotide sequence encoding the polypeptide of claim 1, which results in the mutant producing less of the polypeptide than the parent cell.

12. A mutant cell produced by the method of claim 11.

13. A method of producing the polypeptide of claim 1, comprising: (a) cultivating a transgenic plant or a plant cell comprising a polynucleotide encoding the polypeptide under conditions conducive for production of the polypeptide; and (b) recovering the polypeptide.

14. A transgenic plant, plant part or plant cell transformed with a polynucleotide encoding the polypeptide of claim 1.

15. A method for degrading a xylan-containing material, comprising treating the xylan-containing material with the polypeptide having acetylxylan esterase activity of claim 1.

16. The method of claim 15, further comprising treating the xylan-containing material with a xylan degrading enzyme.

17. A composition comprising the polypeptide of claim 1.

18. The polypeptide of claim 2, wherein the mature polypeptide is 20 to 377 of SEQ ID NO: 2.

19. The polynucleotide of claim 6, comprising at least one mutation in the mature polypeptide coding sequence of SEQ ID NO: 1, in which the mutant nucleotide sequence encodes the mature polypeptide of SEQ ID NO: 2.

20. A recombinant expression vector comprising the nucleic acid construct of claim 7.

* * * * *

SEQUENCE LISTING

<160> NUMBER OF SEQ ID NOS: 11

<210> SEQ ID NO 1
<211> LENGTH: 1269
<212> TYPE: DNA
<213> ORGANISM: Humicola insolens

<400> SEQUENCE: 1

```
atgaaggtcc cgactctcat ctcgagcctc ctggctctgg tctccttctc cgaggccacg      60
ccgctcatca agcgagcgac gctcacgcgg gtcaacaact tcggtaacaa ccctagcggt     120
gcgcgcatgt acatctatgt gcccgacagg cttcagccac gtcctgccgt tctcacggcc     180
gttcactact gcacgggcac cgccaacgcc ttctacaccg gtactccgta tgctcgtctt     240
gccgaccagt atggcttcat tgtcgtctac ccggagtctc ccaataacgg cggttgctgg     300
gatgtctcgt cccgcgctgc ctacacccgc gatagcggtt ccaacagcca cgccatttct     360
ctcatgacga agtgggctct gcagcaatat aatggtgacc cagagaaggt ctttgttgcc     420
ggcaccagct cgggcgctat gatgacggtg agtgacacag agatgaggct caagttgtgg     480
tcagctacct tgtcccggtt actgacacct gtctcaccag aatgttctct ctgctgtgta     540
ccctgatctg tacaaggctg ccgctgccta cgctggtgtc cctgcgggct gcttctacac     600
gggcactgtt gctggctgga actcgacttg cgccaacggc cagtccatta ccactcagga     660
acactgggcc aggacggcgc tcgatatgta ccctggctac accggcccgc gtccacgcat     720
gctcatctac cacggctccg ctgacacgac catctatcct cgggtaagcc ctatgccccc     780
caaaaagcag gctattggac ctccaataac tgacaaccgc cgcagaactt caacgagact     840
ctgaagcagt gggccggcgt tttcggttac acttacggcc agcctcagca gaccctcccc     900 aacacccgt cggcgcctta caccaagtat gtctacggcc ccaacctcgt cggcatctac     960
ggcagcggcg tcacccacaa catccccgtc aacggcgcca acgacatgga atggttcggc    1020
atcaccggca acccgaccac cacctcgacg tctgctactg tgcctactac cacgagcagc    1080
cccggcacca cctcgaccag cgcccggtc accacgacca cctcccgggc tcctcccct     1140
```

```
cctacccaga cttgtatacc cgttcctcgt tggggccagt gcggcggcat cacctgggga    1200
ggctgcacgg tgtgcgaggc gccgtacact tgccagaagc tgaatgattg gtactctcag    1260
tgcctgtaa                                                            1269
```

<210> SEQ ID NO 2
<211> LENGTH: 377
<212> TYPE: PRT
<213> ORGANISM: Humicola insolens

<400> SEQUENCE: 2

```
Met Lys Val Pro Thr Leu Ile Ser Ser Leu Leu Ala Leu Val Ser Phe
1               5                   10                  15

Ser Glu Ala Thr Pro Leu Ile Lys Arg Ala Thr Leu Thr Arg Val Asn
                20                  25                  30

Asn Phe Gly Asn Asn Pro Ser Gly Ala Arg Met Tyr Ile Tyr Val Pro
            35                  40                  45

Asp Arg Leu Gln Pro Arg Pro Ala Val Leu Thr Ala Val His Tyr Cys
        50                  55                  60

Thr Gly Thr Ala Asn Ala Phe Tyr Thr Gly Thr Pro Tyr Ala Arg Leu
65                  70                  75                  80

Ala Asp Gln Tyr Gly Phe Ile Val Val Tyr Pro Glu Ser Pro Asn Asn
                85                  90                  95

Gly Gly Cys Trp Asp Val Ser Ser Arg Ala Ala Tyr Thr Arg Asp Ser
            100                 105                 110

Gly Ser Asn Ser His Ala Ile Ser Leu Met Thr Lys Trp Ala Leu Gln
        115                 120                 125

Gln Tyr Asn Gly Asp Pro Glu Lys Val Phe Val Ala Gly Thr Ser Ser
    130                 135                 140

Gly Ala Met Met Thr Asn Val Leu Ser Ala Val Tyr Pro Asp Leu Tyr
145                 150                 155                 160

Lys Ala Ala Ala Ala Tyr Ala Gly Val Pro Ala Gly Cys Phe Tyr Thr
                165                 170                 175

Gly Thr Val Ala Gly Trp Asn Ser Thr Cys Ala Asn Gly Gln Ser Ile
            180                 185                 190

Thr Thr Gln Glu His Trp Ala Arg Thr Ala Leu Asp Met Tyr Pro Gly
        195                 200                 205

Tyr Thr Gly Pro Arg Pro Arg Met Leu Ile Tyr His Gly Ser Ala Asp
    210                 215                 220

Thr Thr Ile Tyr Pro Arg Asn Phe Asn Glu Thr Leu Lys Gln Trp Ala
225                 230                 235                 240

Gly Val Phe Gly Tyr Thr Tyr Gly Gln Pro Gln Gln Thr Leu Pro Asn
                245                 250                 255

Thr Pro Ser Ala Pro Tyr Thr Lys Tyr Val Tyr Gly Pro Asn Leu Val
            260                 265                 270

Gly Ile Tyr Gly Ser Gly Val Thr His Asn Ile Pro Val Asn Gly Ala
        275                 280                 285

Asn Asp Met Glu Trp Phe Gly Ile Thr Gly Asn Pro Thr Thr Thr Ser
    290                 295                 300

Thr Ser Ala Thr Val Pro Thr Thr Ser Ser Pro Gly Thr Thr Ser
305                 310                 315                 320

Thr Ser Ala Pro Val Thr Thr Thr Ser Arg Ala Pro Pro Pro
                325                 330                 335

Thr Gln Thr Cys Ile Pro Val Pro Arg Trp Gly Gln Cys Gly Gly Ile
            340                 345                 350
```

```
Thr Trp Gly Gly Cys Thr Val Cys Glu Ala Pro Tyr Thr Cys Gln Lys
        355                 360                 365
Leu Asn Asp Trp Tyr Ser Gln Cys Leu
    370                 375
```

<210> SEQ ID NO 3
<211> LENGTH: 13
<212> TYPE: PRT
<213> ORGANISM: Humicola insolens

<400> SEQUENCE: 3

```
Ala Ser Leu Gln Gln Val Trp Asn Trp Gly Ala Asn Pro
1               5                   10
```

<210> SEQ ID NO 4
<211> LENGTH: 9
<212> TYPE: PRT
<213> ORGANISM: Humicola insolens

<400> SEQUENCE: 4

```
Asn Ser Tyr Pro Gly Tyr Asx Gly Arg
1               5
```

<210> SEQ ID NO 5
<211> LENGTH: 33
<212> TYPE: DNA
<213> ORGANISM: Humicola insolens
<220> FEATURE:
<221> NAME/KEY: misc_feature
<222> LOCATION: (1)..(1)
<223> OTHER INFORMATION: w = a or t
<220> FEATURE:
<221> NAME/KEY: misc_feature
<222> LOCATION: (2)..(2)
<223> OTHER INFORMATION: s = c or g
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: y = c or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: r = a or g
<220> FEATURE:
<221> NAME/KEY: misc_feature
<222> LOCATION: (12)..(12)
<223> OTHER INFORMATION: r = a or g
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: y = c or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)

```
<223> OTHER INFORMATION: y = c or t

<400> SEQUENCE: 5
wsnytncarc argtntggaa ytggggngcn aay                             33

<210> SEQ ID NO 6
<211> LENGTH: 10
<212> TYPE: PRT
<213> ORGANISM: Humicola insolens
<220> FEATURE:
<221> NAME/KEY: MISC_FEATURE
<222> LOCATION: (1)..(1)
<223> OTHER INFORMATION: XAA=Any amino acid
<220> FEATURE:
<221> NAME/KEY: MISC_FEATURE
<222> LOCATION: (2)..(2)
<223> OTHER INFORMATION: XAA=Any amino acid

<400> SEQUENCE: 6

Xaa Xaa Gln Gln Val Trp Asn Trp Gly Ala
1               5                   10

<210> SEQ ID NO 7
<211> LENGTH: 25
<212> TYPE: DNA
<213> ORGANISM: Humicola insolens
<220> FEATURE:
<221> NAME/KEY: misc_feature
<222> LOCATION: (14)..(14)
<223> OTHER INFORMATION: r= a or g
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: r= a or g

<400> SEQUENCE: 7
ggcggcggcc gtcrtanccn ggrta                                     25

<210> SEQ ID NO 8
<211> LENGTH: 27
<212> TYPE: DNA
<213> ORGANISM: Humicola insolens

<400> SEQUENCE: 8
ctacacgggc actgttgctg gctggaa                                   27

<210> SEQ ID NO 9
<211> LENGTH: 27
<212> TYPE: DNA
<213> ORGANISM: Humicola insolens

<400> SEQUENCE: 9
acactgggcc aggacggcgc tcgatat                                   27

<210> SEQ ID NO 10
<211> LENGTH: 36
<212> TYPE: DNA
<213> ORGANISM: Humicola insolens

<400> SEQUENCE: 10
acacaactgg ccatgaaggt cccgactctc atctcg                         36
```

```
<210> SEQ ID NO 11
<211> LENGTH: 36
<212> TYPE: DNA
<213> ORGANISM: Humicola insolens

<400> SEQUENCE: 11
cagtcacctc tagttattac aggcactgag agtacc                                36
```